(12) United States Patent
Lin

(10) Patent No.: US 10,385,463 B2
(45) Date of Patent: Aug. 20, 2019

(54) GAS GENERATOR

(71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 0 days.

(21) Appl. No.: 15/684,147

(22) Filed: Aug. 23, 2017

(65) Prior Publication Data

US 2018/0057948 A1    Mar. 1, 2018

(30) Foreign Application Priority Data

Aug. 24, 2016 (CN) .......................... 2016 1 0718226

(51) Int. Cl.

| | |
|---|---|
| *C25B 15/02* | (2006.01) |
| *C25B 1/00* | (2006.01) |
| *C25B 9/18* | (2006.01) |
| *C25B 1/06* | (2006.01) |
| *C25B 3/02* | (2006.01) |
| *C25B 1/04* | (2006.01) |
| *C25B 15/08* | (2006.01) |
| *C25B 9/10* | (2006.01) |
| *A61M 16/12* | (2006.01) |
| *H01R 13/648* | (2006.01) |

(52) U.S. Cl.
CPC ............. *C25B 1/04* (2013.01); *A61M 16/125* (2014.02); *C25B 9/10* (2013.01); *C25B 15/08* (2013.01); *A61M 2202/0007* (2013.01); *A61M 2202/02* (2013.01); *A61M 2205/0233* (2013.01); *H01R 13/6485* (2013.01); *Y02E 60/366* (2013.01)

(58) Field of Classification Search
CPC .. C25B 15/02; C25B 1/04; C25B 1/00; C25B 9/00; C25B 9/18; C25B 1/02; C25B 1/06; C25B 3/02
USPC .................................. 205/752, 755; 204/232
See application file for complete search history.

(56) References Cited

U.S. PATENT DOCUMENTS

| | | | |
|---|---|---|---|
| 2005/0000802 A1* | 1/2005 | Hobbs ...................... | C01B 3/34 |
| | | | 204/277 |
| 2007/0272548 A1* | 11/2007 | Sutherland ................ | C25B 1/04 |
| | | | 204/242 |
| 2014/0048067 A1* | 2/2014 | McGill ................. | A61M 16/10 |
| | | | 128/203.29 |

FOREIGN PATENT DOCUMENTS

TW             201113224 A     4/2011

* cited by examiner

*Primary Examiner* — Zulmariam Mendez
(74) *Attorney, Agent, or Firm* — Klintworth & Rozenblat IP LLP

(57) ABSTRACT

The present invention provides a gas generator and comprises an electrolytic cell, a gas pathway, and an anti-static device. The electrolytic cell is for electrolyzing electrolyzed water to generate a gas with hydrogen. The gas generated from the electrolytic cell is transferred by the gas pathway. The anti-static device is set in the gas generator for reducing or eliminating the static electricity. The present invention uses the anti-static device to prevent the gas with hydrogen in the gas pathway from exploding by the static electricity, thereby providing a safe gas generator.

10 Claims, 5 Drawing Sheets

GAS GENERATOR

CROSS-REFERENCE TO RELATED APPLICATIONS

This application claims priority to Chinese Application No. 201610718226.4, filed Aug. 24, 2016, hereby incorporated herein by reference in its entirety.

BACKGROUND OF THE INVENTION

1. Field of the Invention

The present invention relates to a gas generator, and more particularly, to a gas generator with an anti-static device.

2. Description of the Prior Art

As people have always been paying much attention on health developments, many developments in medical technology are often targeted on treating diseases and prolonging human life. Also, most of the treatments in the past are passive; it is meant that the disease is treated only when it occurs. The treatments include an operation, a medication treatment, a radiation therapy, or a medical treatment for cancer. However, in recent years, most of the medical experts' researches are gradually moving towards preventive medical methods, such as research on healthy food, screening and the prevention of inherited diseases, and prevent diseases from occurring in the future actively. Due to the focus of the prolongation of human life, many anti-aging and anti-oxidation technologies including skin care products and anti-oxidation food/medicine are gradually being developed. Moreover, those products are becoming increasingly popular to the general public.

Studies have found that there are instable oxygen species ($O^+$), also known as free radicals, in the human body. The free radicals which are usually generated due to diseases, diet, environment and one's lifestyle can be excreted in the form of water by reacting with the inhaled hydrogen. With this method, the amount of free radicals in the human body can be reduced, thereby the body condition returns from an acidic state to an alkaline state. Also, the purpose of anti-oxidation, anti-aging and beauty health effect, and even eliminating chronic diseases can be achieved. Furthermore, there are also clinical experiments showing that patients who need to inhale a high concentration of oxygen for an extended period of time would experience lung damage. However, they could be ameliorated by inhaling hydrogen.

However, the gas with hydrogen produced by the electrolysis of the electrolytic water is usually flammable if the hydrogen concentration is high. Any electrostatic sparks are likely to ignite and cause gas explosion, thereby resulting in the use of electrolytic cell in danger.

SUMMARY OF THE INVENTION

The present invention is to provide a gas generator for electrolyzing water to produce a gas with hydrogen and mixing the gas with hydrogen with an atomized gas to generate a healthy gas for human to inhale. Besides, an anti-static device is set in the gas generator for reducing or eliminating the static electricity in the gas generator to reduce the possibility of the explosion of the gas with hydrogen.

The gas generator of the present invention comprises the electrolytic cell, a gas pathway and the anti-static device. The electrolytic cell accommodates the electrolyzed water comprising an electrolyte. The electrolytic cell is configured for electrolyzing the electrolyzed water to generate the gas with hydrogen. The gas pathway is connected to the electrolytic cell for transferring the gas with hydrogen. The anti-static device is set in the gas generator for reducing or eliminating the static electricity in the gas generator.

The gas pathway comprises a pathway inlet for being connected to the electrolytic cell, and the anti-static device is set on the gas pathway.

The gas generator comprises an atomization device connected to the gas pathway for generating an atomized gas and receiving the gas with hydrogen to mix the atomized gas with the gas with hydrogen to generate a healthy gas.

The gas generator comprises an outlet for outputting the healthy gas, and the anti-static device is set between the pathway inlet and the outlet.

The anti-static device is set between the atomization device and the electrolytic cell.

The anti-static device is set on the electrolytic cell. For example, the electrolytic cell comprises a gas storage part accommodating the gas with hydrogen, and the anti-static device is set on the gas storage part.

The anti-static device comprises a ground terminal, and the ground terminal is connected to the earth.

To summarize, the object of the present invention is to provide a gas generator comprising an electrolytic cell, a gas pathway and an anti-static device. In the gas generator of the present invention, the gas with hydrogen generated by the electrolytic cell is transferred by the gas pathway for human to breathe in. And an anti-static device is provided in the gas generator for reducing or eliminating the static electricity in the gas generator to reduce the possibility of the explosion of the gas with hydrogen.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1A:
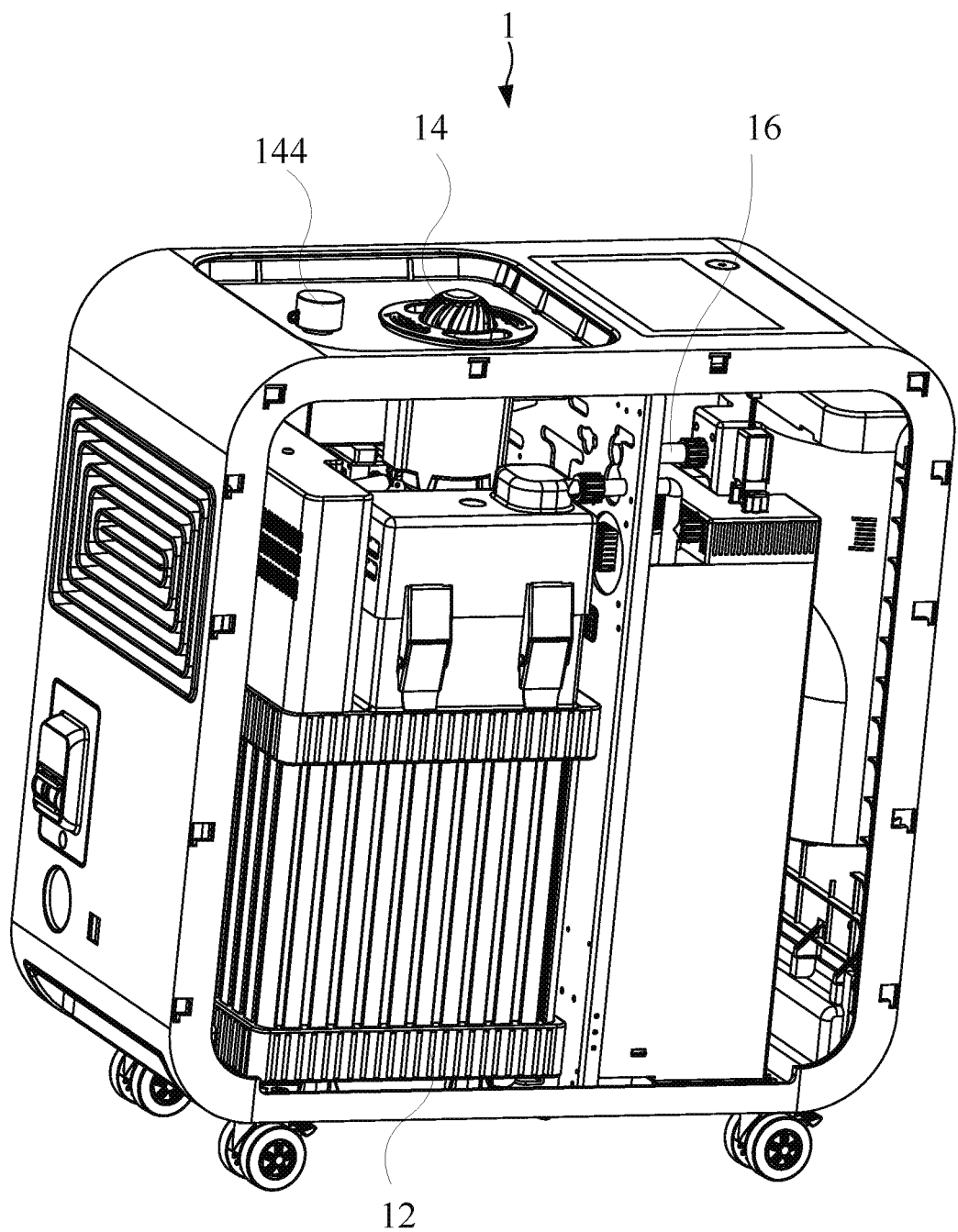
FIG. 1A and FIG. 1B show a schematic diagram of the gas generator in an embodiment with different visual angles of the present invention.
Figure 1B:
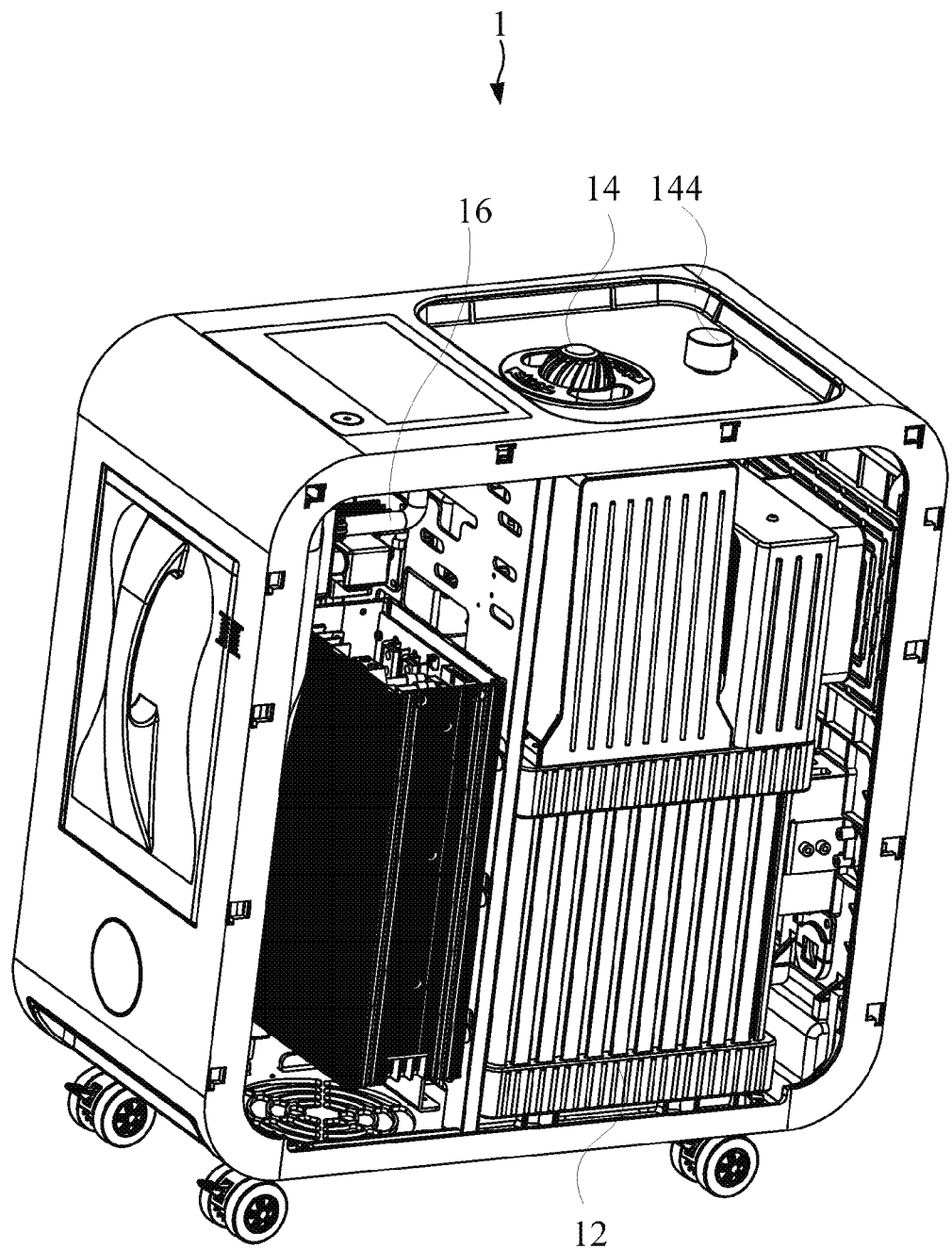
Figure 2:
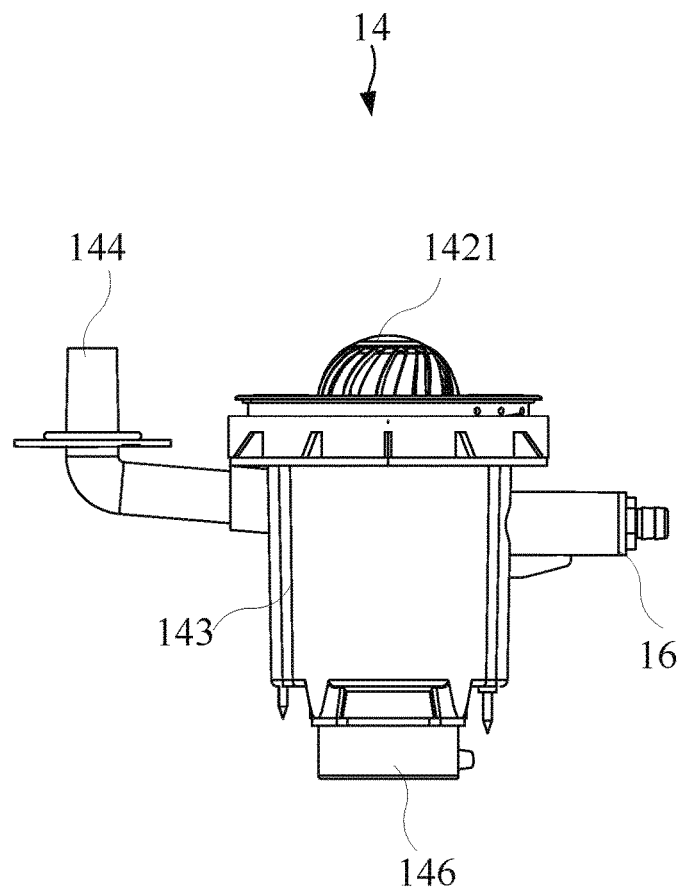
FIG. 2 illustrates a schematic diagram of the atomization device of the gas generator in an embodiment of the present invention.
Figure 3:
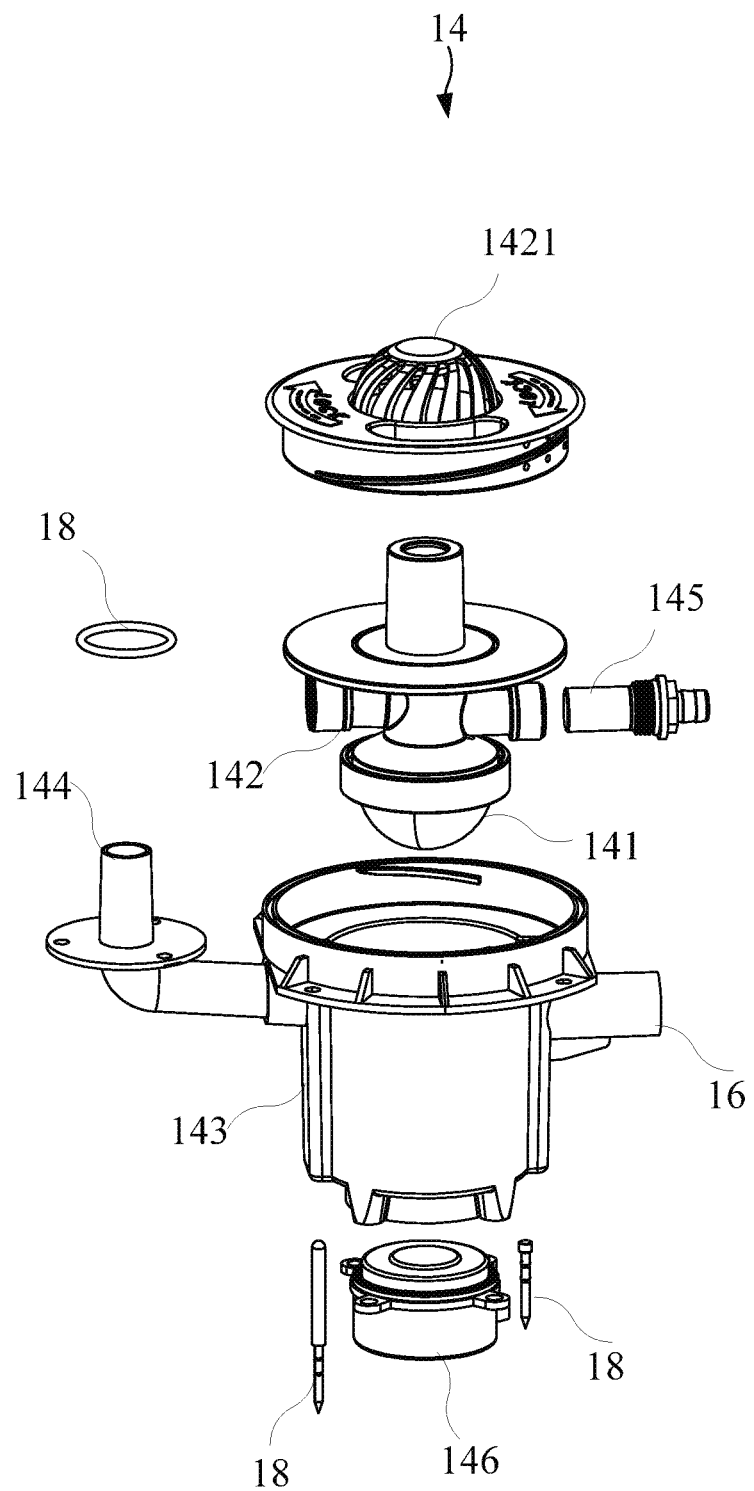
FIG. 3 illustrates an explosion diagram of the atomization device of the gas generator in an embodiment of the present invention.

Please refer to FIG. 1A, FIG. 1B, FIG. 2, and FIG. 3. FIG. 1A and FIG. 1B show a schematic diagram of the gas generator 1 in an embodiment with different visual angles of the present invention. FIG. 2 illustrates a schematic diagram of the atomization device 14 of the gas generator 1 in an embodiment of the present invention. FIG. 3 illustrates an explosion diagram of the atomization device 14 of the gas generator 1 in an embodiment of the present invention. The gas generator 1 of the present invention comprises an electrolytic cell 12, a gas pathway 16 and an anti-static device 18. The electrolytic cell 12 accommodates the electrolyzed water comprising an electrolyte. The electrolytic cell 12 is configured for electrolyzing the electrolyzed water to generate the gas with hydrogen. The gas pathway 16 is connected to the electrolytic cell 12 for transferring the gas with hydrogen. The anti-static device 18 is set in the gas generator 1 for reducing or eliminating the static electricity in the gas generator 1.

The gas pathway 16 comprises a pathway inlet for being connected to the electrolytic cell 12, and the anti-static device 18 is set on the gas pathway 16.

Figure 4:
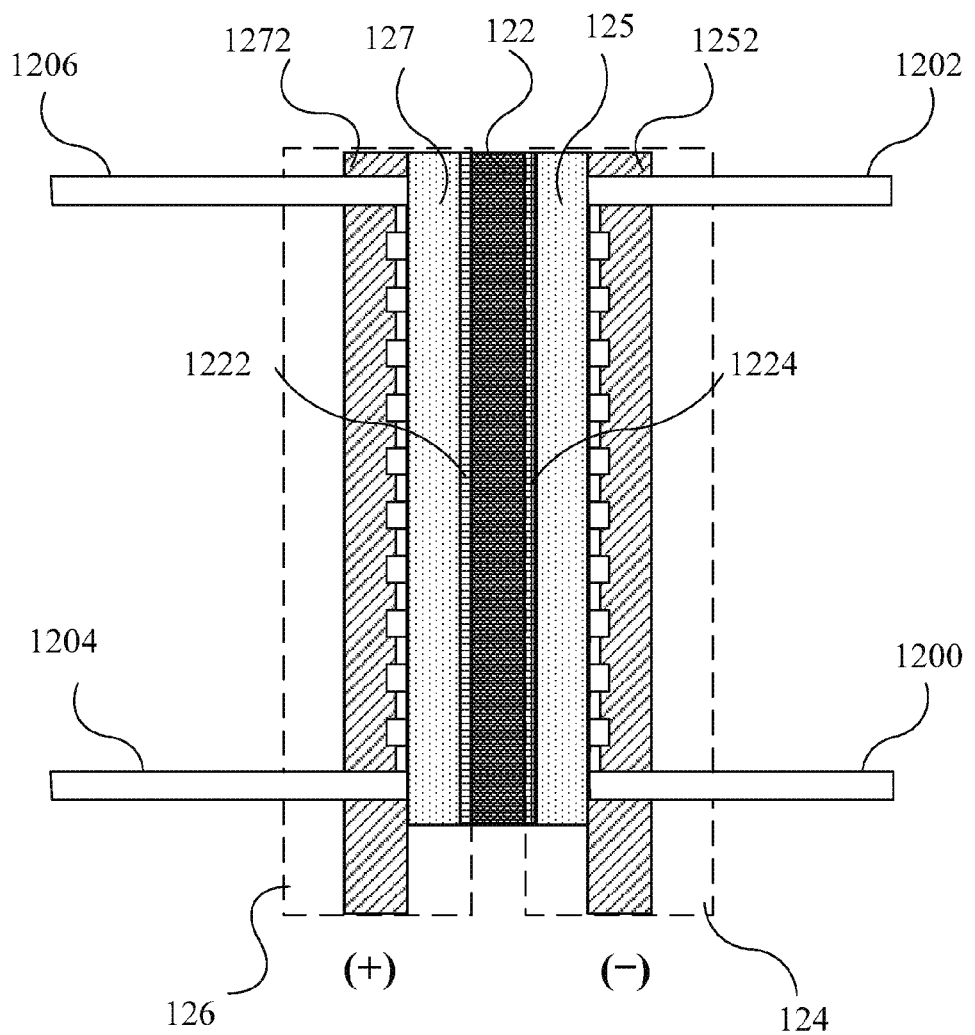
FIG. 4 illustrates a schematic diagram of the ion membrane electrolytic cell of the gas generator in an embodiment of the present invention.

Please refer to FIG. 4. FIG. 4 illustrates a schematic diagram of the ion membrane electrolytic cell 12 of the gas generator 1 in an embodiment of the present invention. In an embodiment, the electrolytic cell 12 comprises an ion membrane electrolytic device. And the ion membrane electrolytic device comprises an ion exchange membrane 122, a cathode chamber 124 and an anode chamber 126. The cathode electrode 125 is set in the cathode chamber 124 and the anode electrode 127 is set in the anode chamber 126 shown in FIG. 4 (for the sake of clarity, the anode chamber 126 and the cathode chamber 124 are indicated by a dotted line). The ion exchange membrane 122 is set between the anode chamber 126 and the cathode chamber 124. Oxygen is generated by the anode electrode 127 and hydrogen is generated by the cathode electrode 125 when the ion membrane electrolytic device electrolyzes water. In an embodiment, water is contained in the anode chamber 126 and water in the anode chamber 126 may, but not limited to, further penetrate into the cathode chamber 124 through the ion exchange membrane 122. In another embodiment, the anode chamber 126 and the cathode chamber 124 can accommodate water at the same time. The anode electrode 127 can electrolyze water to generate hydrogen ion and oxygen. The hydrogen ion can penetrate through the ion exchange membrane 122 to the cathode chamber 124, and hydrogen is generated on the cathode electrode 125 after getting the electrode. In practice, hydrogen can be generated, but not limited to, on the catalyst layer; hydrogen can also be generated on the electrode plate or between the ion membrane and the electrode plate.

Besides, the ion membrane electrolytic device comprises a cathode current-conducting plate 1252 and an anode current-conducting plate 1272. The anode electrode 127 or the cathode electrode 125 of the ion membrane electrolytic device can be connected with an external power source by the cathode current-conducting plate 1252 and the anode current-conducting plate 1272. Furthermore, the ion membrane electrolytic device can further comprise a gas tube 1200, and the gas tube 1200 can connect the cathode chamber 124 and the outside. The ion membrane electrolytic device can further comprise the hydrogen tube 1202 connected to the cathode chamber 124 to transfer the gas with hydrogen into the gas pathway 16. The ion membrane electrolytic device can further comprise a water supply tube 1204 to recharge water from the electrolytic cell 12 into the cathode chamber 124 and the anode chamber 126. The ion membrane electrolytic device can further comprise an oxygen tube 1206 connected with the anode chamber 126 to output oxygen to the outside from the electrolytic cell 12. Besides, the ion membrane electrolytic device can further comprise a ratio regulator (not shown) connected with the hydrogen tube 1202 and the gas pathway 16, and is further connected with the gas tube 1200 or the oxygen tube 1206. Therefore, the hydrogen concentration is regulated to generate the gas with hydrogen as-needed and then the gas with hydrogen is transferred to the gas pathway 16.

In practical application, the ion exchange membrane 122 further comprises an anode catalyst layer 1222 and a cathode catalyst layer 1224. The anode catalyst layer 1222 can be selected from a group consisting of Pt, Ir, Pd, the alloy powder of Pt, carbon, or any combination thereof. The cathode catalyst layer 1224 can be selected from a group consisting of Pt, Ir, Pd, the alloy powder of Pt, or any combination thereof. In an embodiment, the material of the anode catalyst layer 1222 or the cathode catalyst layer 1224 can be configured into slurry to be coated on the both sides of the ion membrane to form the anode catalyst layer 1222 and the cathode catalyst layer 1224.

Gas generator 1 can further comprise an atomization device 14 connected to the gas pathway 16 for generating an atomized gas and receiving the gas with hydrogen. Then the atomization device 14 mixes the atomized gas with the gas with hydrogen to generate a healthy gas. The atomization device 14 comprises an atomizing chamber 141 and a mixing reaction chamber 142. The atomizing chamber 141 is configured for generating the atomized gas. The mixing reaction chamber 142 is connected to the gas pathway 16 and the atomizing chamber 141 respectively, for receiving the gas with hydrogen to mix the atomized gas with the gas with hydrogen to generate the healthy gas. Wherein, the capacity of the mixing reaction chamber 142 is smaller than the capacity of the atomizing chamber 141.

Wherein, the anti-static device 18 is set on the atomization device 14.

Furthermore, the anti-static device 18 is set between the atomization device 14 and the electrolytic cell 12.

The gas pathway 16 comprises a pathway inlet connected to the electrolytic cell 12; the gas generator 1 comprises an outlet for outputting the healthy gas, and the anti-static device 18 is set between the pathway 16 inlet and the outlet.

In practical application, the atomization device 14 can further comprise a shaker 146 for oscillating the atomized gas precursor in the atomizing chamber 141 into the atomized gas as-needed. The atomized gas is selected from one of the groups consisting of water vapor, atomized solution, volatile essential oil and combinations thereof.

In practical application, the atomization device 14 can further comprise an atomization device shell 143 for fixing the position of the other parts of the atomization device 14.

In addition, the atomization device 14 comprises a healthy gas outlet 144 for the user to breathe the healthy gas. In practice, the atomization device 14 can further comprise a gas communication tube 145 for connecting the mixing reaction chamber 142 and the gas pathway 16.

The gas pathway 16 has a flow channel inlet configured for the connection to the electrolytic cell 12. The anti-static device 18 is set on the flow channel inlet. Also, the anti-static device 18 is integrally formed on the flow channel inlet.

The anti-static device 18 comprises a ground terminal, and the ground terminal is connected to the earth.

In practice, the anti-static device 18 can be a material capable of transferring charge such as a metal mesh, a metal sheet or a metal film, or constituted by a conductive member such as a screw, a wire or a spacer. At the same time, the anti-static device 18 can be partially or completely disposed at the before-mentioned position to be set. Also, the anti-static device 18 can be completely or partially disposed in the preset device.

In an embodiment, the anti-static device 18 comprises a metal ring on the flow channel inlet and outlet. The anti-static device 18 further comprises a ground wire connected to the metal ring, and the other end of the ground wire is grounded to balance the metal ring charge.

In another embodiment, the anti-static device 18 can be a metal clip placed in a gas contact surface of the removable atomization device 14 and the gas pathway 16 and fixed to a conductive shell. Thereby, the relative position of the atomization device 14 and the gas pathway 16 can be fixed. Meanwhile, the charge distribution of the passing gas can be balanced.

In another embodiment, the anti-static device 18 can even be a metal film. The anti-static device 18 is coated on the entire gas pathway of the gas generator 1. The charge distribution of the gas contained within the gas generator 1 can be balanced to reduce or eliminate the generation of the static electricity in the gas generator 1.

The electrolytic cell 12 comprises a gas storage part accommodating the gas with hydrogen, and the anti-static device 18 is set on the gas storage part. The gas storage portion described herein is a place of the gas with hydrogen electrolyzed by the electrolytic cell 12 flowing through.

Besides, the anti-static device 18 can be set on the atomization device 14 or the gas pathway 16.

Please refer to FIG. 3 again. In the present embodiment, the anti-static device 18 is set on the atomization device shell 143. The anti-static device 18 is set on the interface between the shell and the gas with hydrogen. The atomization device shell 143 is connected to the shell of the gas generator 1 of the present invention and grounded. Therefore, the gas with hydrogen ignited by the static electricity is prevented.

In addition, the anti-static device 18 can be set on the healthy gas outlet 144 to prevent the healthy gas from being ignited by static electricity when the healthy gas is exhausted. Therefore, the user's injury caused by the ignition of the gas during breathing-in can be avoided.

The gas generator 1 further comprises a draw tube connected to the atomization device for transferring the healthy gas, and the anti-static device 18 is set in the draw tube.

Wherein, the draw tube can further comprise a draw mask for the user to press closely to the nose and the mouth to breathe in the healthy gas.

In practice, the mixing reaction chamber 142 further comprises an explosion-proof aperture 1421 for preventing the gas with hydrogen from exploding within the gas pathway 16. The explosion-proof aperture 1421 can be composed of a soft silicone. If it is unfortunate that the gas explosion occurs in the gas generator 1, the gas can be escaped from the most vulnerable explosion-proof aperture 1421. Thereby preventing the remaining parts of the machine of the gas generator 1 from being damaged by air pressure or high temperature flame, nor causing the exudation of the electroplating solution or the damage of the control circuit board due to the gas explosion.

In summary, in the gas generator of the present invention, the gas with hydrogen generated by the electrolytic device is transferred by the gas pathway for human to breathe in. And an anti-static device is set in the gas generator for reducing or eliminating the static electricity in the gas generator to reduce the possibility of the explosion of the gas with hydrogen.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator, comprising:
   an electrolytic cell, accommodating an electrolyzed water comprising an electrolyte, for electrolyzing the electrolyzed water to generate a gas comprising hydrogen and oxygen, the electrolytic cell comprising a gas storage part accommodating the gas comprising hydrogen and oxygen;
   a gas pathway, connected to the electrolytic cell, for transferring the gas comprising hydrogen and oxygen;
   an atomization device, vertically spaced apart from the electrolytic cell and connected to the gas pathway for generating an atomized gas and receiving the gas comprising hydrogen and oxygen to mix the atomized gas with the gas comprising hydrogen and oxygen to generate a healthy gas for human to inhale, the atomization device comprising an atomizing chamber and a mixing reaction chamber, and the atomizing chamber being configured for generating the atomized gas, and the mixing reaction chamber being configured for receiving the gas comprising hydrogen and oxygen to mix the atomized gas with the gas comprising hydrogen and oxygen to generate the healthy gas; and
   an anti-static device, set in the gas generator, for reducing or eliminating the static electricity in the gas generator.

2. The gas generator of claim 1, wherein the gas pathway comprises a pathway inlet for being connected to the electrolytic cell, and the anti-static device is set on the gas pathway.

3. The gas generator of claim 1, wherein the anti-static device is set on the atomization device.

4. The gas generator of claim 1, wherein the anti-static device is set between the atomization device and the electrolytic cell.

5. The gas generator of claim 1, wherein the gas pathway comprises a pathway inlet connected to the electrolytic cell, and the gas generator comprises an outlet for outputting the healthy gas, and the anti-static device is set between the pathway inlet and the outlet.

6. The gas generator of claim 1, wherein the anti-static device comprises a ground terminal and the ground terminal is connected to the earth.

7. The gas generator of claim 1, wherein the anti-static device is set on the electrolytic cell.

8. The gas generator of claim 7, wherein the anti-static device is set on the gas storage part.

9. The gas generator of claim 1, further comprising a draw tube connected to the atomization device for transferring the healthy gas, and the anti-static device is set in the draw tube.

10. The gas generator of claim 1, wherein the anti-static device is one selected from the group consisting of metal mesh, metal sheet, metal film, metal ring, and metal clip.

* * * * *